US010300050B2

(12) United States Patent
Clarke et al.

(10) Patent No.: US 10,300,050 B2
(45) Date of Patent: May 28, 2019

(54) SUCCINATE SALT OF CYTISINE AND USE THEREOF

(71) Applicant: Achieve Pharma UK Limited, Henley-on-Thames, Oxfordshire (GB)

(72) Inventors: Anthony Clarke, Henley-on-Thames (GB); Richard Allistair Stewart, Henley-on-Thames (GB); Andrew Gareth Willis, Usk (GB)

(73) Assignee: Achieve Pharma UK Limited, Henley-on-Thames (GB)

( * ) Notice: Subject to any disclaimer, the term of this patent is extended or adjusted under 35 U.S.C. 154(b) by 0 days.

(21) Appl. No.: 16/075,902

(22) PCT Filed: Feb. 6, 2017

(86) PCT No.: PCT/GB2017/050294
§ 371 (c)(1),
(2) Date: Aug. 6, 2018

(87) PCT Pub. No.: WO2017/134468
PCT Pub. Date: Aug. 10, 2017

(65) Prior Publication Data
US 2019/0038608 A1 Feb. 7, 2019

(30) Foreign Application Priority Data
Feb. 5, 2016 (GB) .................................. 1602145.3

(51) Int. Cl.
| A61K 31/439 | (2006.01) |
| A61K 9/48 | (2006.01) |
| A61K 47/36 | (2006.01) |
| A61P 25/34 | (2006.01) |
| A61K 9/20 | (2006.01) |
| A61K 47/12 | (2006.01) |

(52) U.S. Cl.
CPC .......... *A61K 31/439* (2013.01); *A61K 9/2059* (2013.01); *A61K 9/48* (2013.01); *A61K 47/12* (2013.01); *A61K 47/36* (2013.01); *A61P 25/34* (2018.01)

(58) Field of Classification Search
None
See application file for complete search history.

(56) References Cited

U.S. PATENT DOCUMENTS

| 5,698,224 | A | 12/1997 | Guittard et al. |
| 5,880,164 | A | 3/1999 | Keenan |
| 6,235,734 | B1 | 5/2001 | O'Neill |
| 9,233,109 | B2 | 1/2016 | Papke et al. |
| 9,387,172 | B2 | 7/2016 | Wahl et al. |
| 9,538,781 | B2 | 1/2017 | Zheng |
| 2005/0159471 | A1 | 7/2005 | Stephenson et al. |
| 2010/0048606 | A1 | 2/2010 | Kozikowski et al. |
| 2016/0199315 | A1 | 7/2016 | Takagi et al. |
| 2017/0209415 | A1 | 7/2017 | McKinney et al. |

FOREIGN PATENT DOCUMENTS

| CN | 101428021 A | 5/2009 |
| CN | 102167680 B | 8/2011 |
| CN | 102952134 B | 3/2013 |
| CN | 103044423 B | 4/2013 |
| CN | 103509021 B | 1/2014 |
| CN | 103588773 B | 2/2014 |
| CN | 104710422 A | 6/2015 |
| CN | 106188057 A | 12/2016 |
| EP | 1 586 320 A1 | 10/2005 |
| EP | 2 957 280 A1 | 12/2015 |
| GB | 2550241 A | 11/2017 |
| RU | 2 228 179 C2 | 5/2004 |
| WO | 2014/001348 A1 | 1/2014 |
| WO | 2014/076680 A1 | 5/2014 |
| WO | 2015/025718 A1 | 2/2015 |
| WO | 2016/060577 A1 | 4/2016 |
| WO | 2018/033742 A2 | 2/2018 |

OTHER PUBLICATIONS

UK Patents Act 1977: Search Report Under Section 17(5), dated Jan. 31, 2019, issued in Application No. GB1812071.7, filed Jul. 24, 2018, 4 pages.
International Search Report and Written Opinion dated May 2, 2017, issued in corresponding International Application No. PCT/GB2017/050294, filed Feb. 6, 2017, 7 pages.

*Primary Examiner* — Kamal A Saeed
(74) *Attorney, Agent, or Firm* — Christensen O'Connor Johnson Kindness PLLC

(57) ABSTRACT

The invention relates to a novel salt of cytisine and pharmaceutical compositions comprising that salt. In particular, the invention relates to a succinate salt of cytisine which displays improved excipient compatibility, permitting the preparation of stable pharmaceutical compositions.

16 Claims, 12 Drawing Sheets

HPLC chromatogram of Cytisine (1mg/mL in Mobile Phase) at 310 nm

Fig 1B

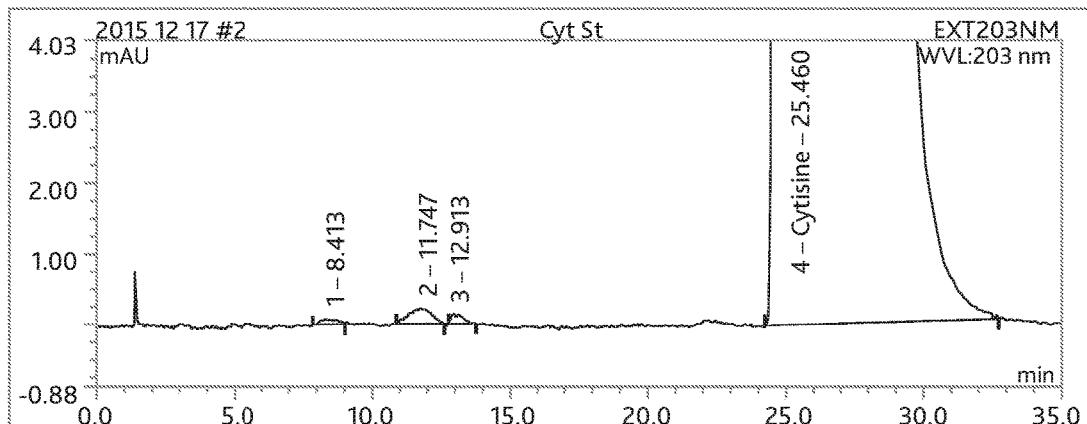

2 Cyt St

13.0mg Cytisine River 20121001C – 10 MPh

| | | | |
|---|---|---|---|
| Sample Name: | Cyt St | Injection Volume: | 20.0 |
| Vial Number: | RA2 | Channel: | EXT203NM |
| Sample Type: | unknown | Wavelength: | 203 |
| Control Program: | Cytisine Salts | Bandwidth: | 0 |
| Quantif. Method: | Cytisine Salts | Dilution Factor: | 1.0000 |
| Run Time (min): | 35.00 | Sample Amount: | 1.0000 |

| No. | Ret.Time min | Peak Name | RRT | Area mAU*min | Asymm | Plates(EP) | Res |
|---|---|---|---|---|---|---|---|
| 1 | 8.41 | n.a. | 0.33 | 0.05599 | 0.98 | 949 | 2.41 |
| 2 | 11.75 | n.a. | 0.46 | 0.22183 | 0.97 | 777 | 0.92 |
| 3 | 12.91 | n.a. | 0.51 | 0.07574 | 2.75 | 3573 | 6.54 |
| 4 | 25.46 | Cytisine | 1.00 | 1153.17886 | 2.09 | 1166 | n.a. |
| Total: | | | 2.299 | 1153.532 | 6.79 | 6465.000 | |

HPLC chromatogram of Cytisine (1mg/mL in Mobile Phase) at 203 nm

HPLC chromatogram of Succinic acid (1mg/mL in Mobile Phase) at 310 nm

HPLC chromatogram of Succinic acid (1mg/mL in Mobile Phase) at 203 nm

HPLC chromatogram of Cytisine Succinate (1mg/mL in Mobile Phase) at 310 nm

HPLC chromatogram of Cytisine Succinate (1mg/mL in Mobile Phase) at 203 nm

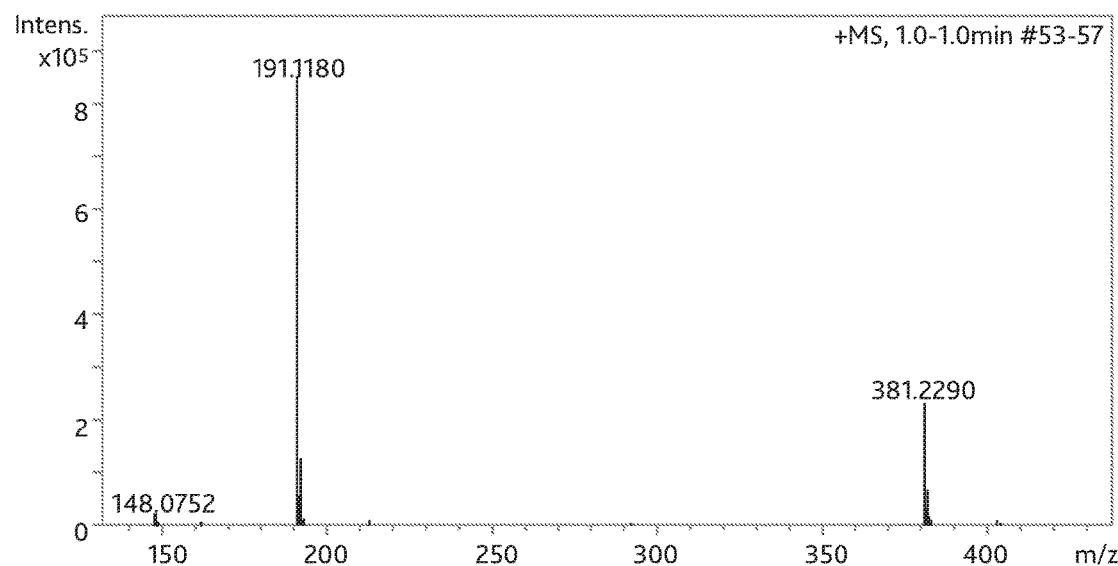
HR ESI+ MS Spectrum of Cytisine Succinate (191.1180 Cyt+H+; 381.2290 2Cyt+H+)
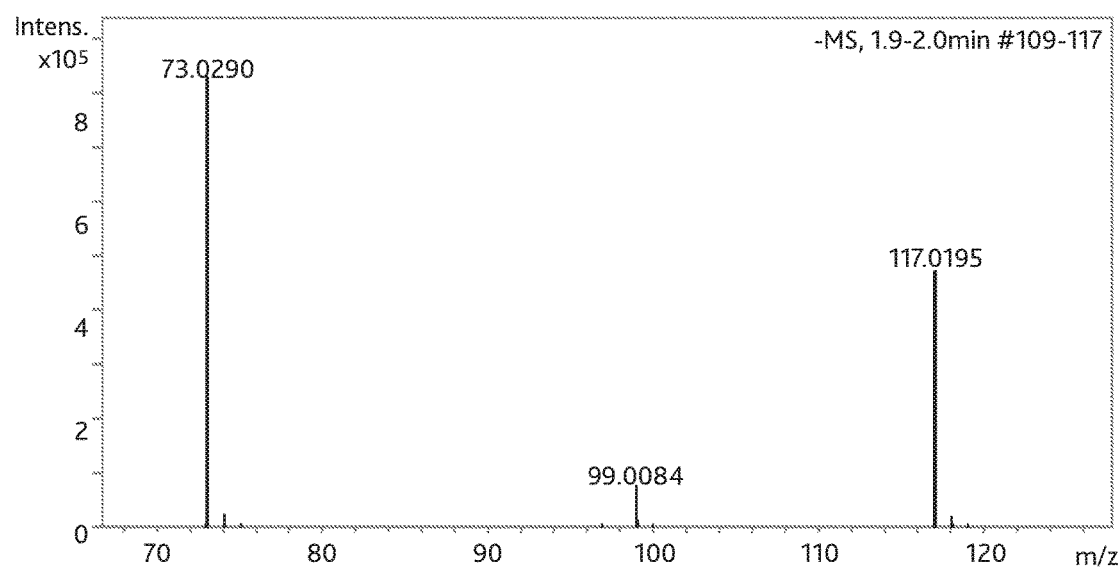
HR ESI- MS Spectrum of Cytisine Succinate (117.0195 Succ-H+; 99.0084 Succ-$H_2O$-H+; 73.0290 Succ-$CO_2$-H+)

HR ESI+ MS/MS Spectrum of 191.1180 (191.1180 Cyt+H$^+$; 148.0754 Cyt-CH$_2$NHCH$_2$+H$^+$)

HR ESI- MS/MS Spectrum of 117.0191 (117.0195 Succ-H$^+$; 99.0084 Succ-H$_2$O-H$^+$; 73.0290 Succ-CO$_2$-H$^+$)

cytisine succinate

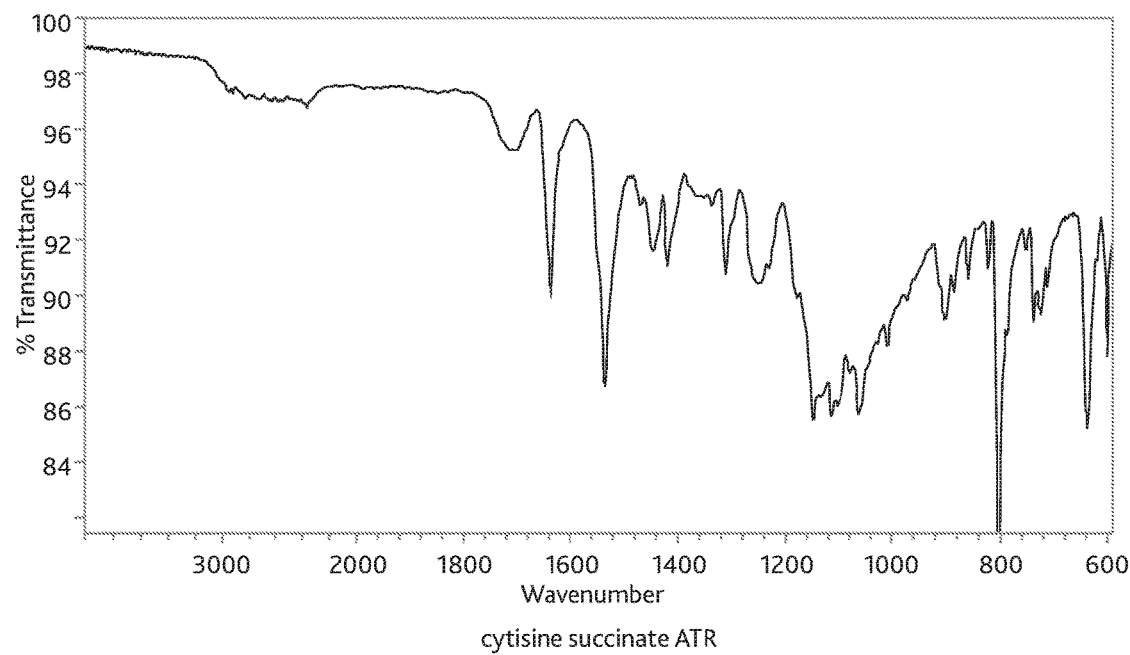

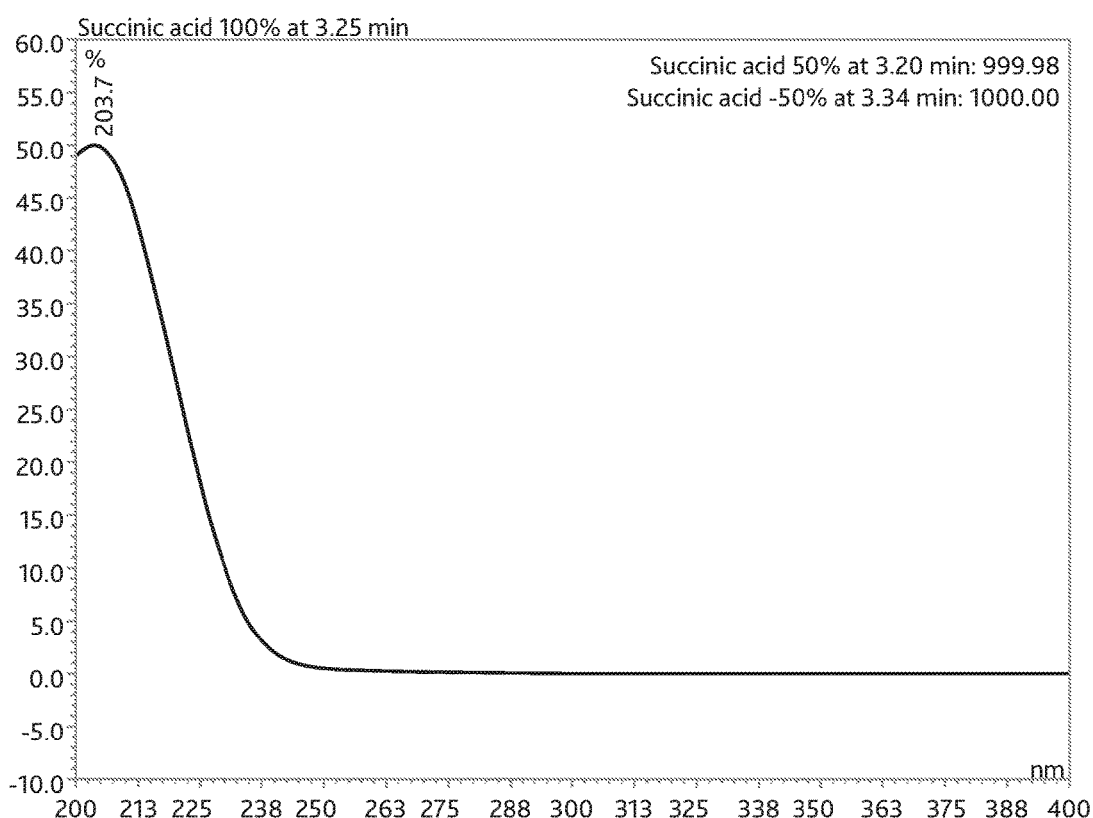
Peak purity of the signal with RT 3,25 min (Succinic acid) and the corresponding UV-VIS spectrum recorded with DAD

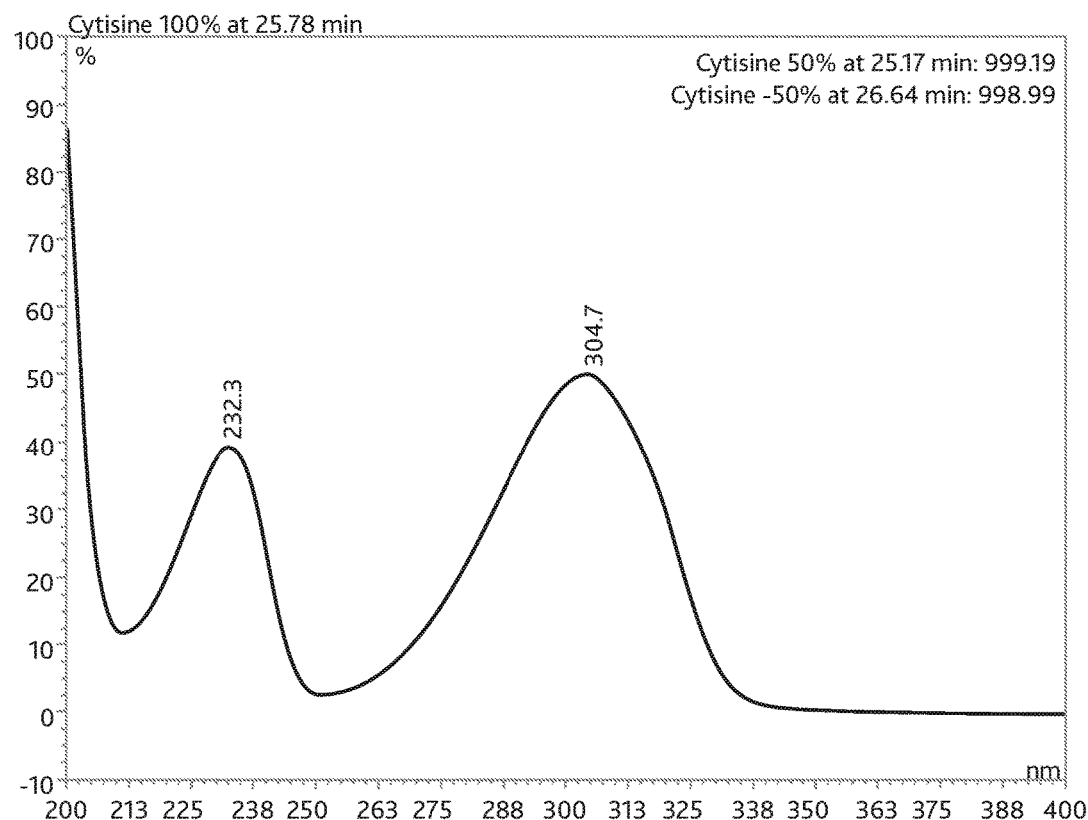
Peak purity of the signal with RT 25,78 min (Cytisine) and the corresponding UV-VIS spectrum recorded with DAD

SUCCINATE SALT OF CYTISINE AND USE THEREOF

The present invention relates to a novel salt of cytisine. The invention also relates to pharmaceutical compositions comprising a novel cytisine salt.

Cytisine is a pyridine-like alkaloid known to be a potent nicotinic acetylcholine receptor agonist. Pharmacologically, cytisine exhibits a high degree of similarity to nicotine.

Numerous studies have indicated that cytisine is useful in the treatment of nicotine addiction.

A pharmaceutical smoking cessation product containing cytisine has been commercialised for several years under the brand name Tabex®. The Tabex® product is marketed in the form of an orally administered tablet comprising 1.5 mg of cytisine free base. While the product has been found to be efficacious and has been commercially successful, the approved shelf life of the product is two years.

As those skilled in the art will recognise, although a two year shelf life for a pharmaceutical product is generally acceptable, it does impose pressure on the manufacturer and supply chain in terms of promptly packaging, transporting and delivering the product to users, and also increases the risk of stock wastage if shelf-life is exceeded. Additionally, where the product is to be shipped to territories with higher temperature/humidity climates (e.g. ICH climactic zones III and IV), then additional packaging to protect the product and maintain shelf-life may be required.

A number of formulation approaches for cytisine-containing products are proposed in the prior art. For example, EP1586320 discloses a solid dosage formulation comprising cytisine free base. While it is stated in that document that the disclosed formulation provides improved stability, there is no suggestion that this could be achieved by the use of salts of cytisine. Indeed, no salts of cytisine are disclosed in that document.

WO2014/076680 discloses a cytisine-containing formulation which again is stated as improving the stability of cytisine. As with EP1586320, there is no suggestion of using a salt of cytisine to improve stability, nor are any salts mentioned. In WO2014/076680 the issue of incompatibility between the cytisine active ingredient and lactose is raised. Specifically, it is stated that lactose may destabilise tablets comprising cytisine due to the presence of a carboxyl group in the lactose molecule, which is not completely inert chemically and may lead to a Maillard reaction.

Accordingly, there is a need in the art for a form of cytisine which inherently is more compatible with conventional excipients such as lactose.

The present inventors have surprisingly and unexpectedly identified a novel salt of cytisine which displays improved excipient compatibility and can be formulated with lactose as an excipient.

Thus, according to a first aspect of the present invention, there is provided a succinate salt of cytisine. In embodiments of the present invention, the salt may be present in the form of a solvate or a hydrate. The salt is preferably cytisine hydrogen succinate.

As mentioned above, the improved compatibility of the salt permits the preparation of stable pharmaceutical compositions. Thus, according to a second aspect of the present invention, there is provided a pharmaceutical composition comprising the succinate salt of cytisine and a pharmaceutically acceptable carrier.

In an embodiment the pharmaceutically acceptable carrier is lactose. The lactose may be lactose monohydrate or anhydrous lactose.

The compositions disclosed herein may be suitable for administration by any route known in the art. Pharmaceutical formulations encompassed within this aspect of the invention include those suitable for oral, nasal or topical administration. In an embodiment, the composition may be formulated in a solid form such as a tablet or a capsule.

In terms of excipients that may be employed in the compositions of the present invention, these include fillers, disintegrants, preserving agents, lubricants (e.g. magnesium stearate) and/or wetting agents. Examples of fillers that may be used include lactose (either anhydrous or monohydrate), cellulose, starch (e.g. corn and/or wheat starch), calcium phosphates, mannitol and others known in the art.

Preserving agents prevent bacterial or fungal contamination of the formulation and may include various antibacterial and antifungal agents such as parabens, chlorobutanol, phenol or sorbic acid.

The pharmaceutical composition may be coated according to any method known in the art, for example using collidone or shellac, gum arabic, talc, titanium dioxide or sugar.

The pharmaceutical compositions of the invention may further comprise sweetening, flavouring or colouring agents.

In embodiments of the invention in which the pharmaceutical composition is provided in the form of capsules, these may be prepared by any suitable method. For example, such capsules may be prepared by mixing the salts with inert carriers such as lactose or sorbitol and packing them into gelatine capsules.

In embodiments of the invention, the pharmaceutical composition will be provided as a unit dosage form (e.g. a tablet, capsule). The amount of cytisine succinate salt in the composition may range from about 0.5 mg or about 1.0 mg to 2.0 mg, 3.0 mg, 5.0 mg or about 10 mg. In embodiments, the pharmaceutical compositions of the present invention may have a shelf life greater than 2 years when stored at 25° C. and at a relative humidity of 60%±5%.

FIGURES

FIG. 4 shows the HR MS spectra of cytisine succinate: (a) ESI+ and (b) ESI−

FIG. 7 shows the peak purity determinations using a DAD detector for cytisine hydrogensuccinate (a) succinic acid and (b) cytisine).

The various embodiments of the present invention will now be further explained with reference to the following examples.

EXAMPLE 1: PREPARATION OF CYTISINE SUCCINATE SALT

Figure 1A:
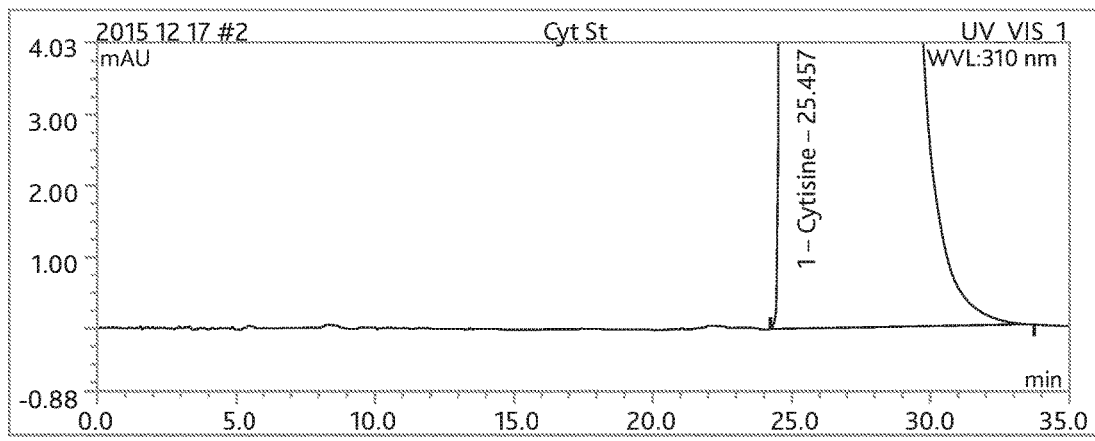
FIG. 1 shows HPLC chromatograms of cytisine at (a) 310 nm and (b) 203 nm.
Figure 2A:
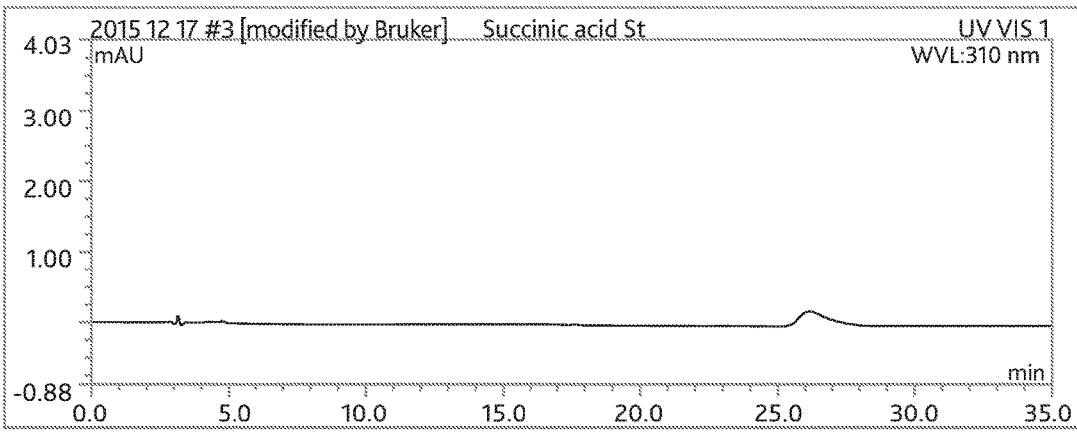
FIG. 2 shows HPLC chromatograms of succinic acid at (a) 310 nm and (b) 203 nm.
Figure 2B:
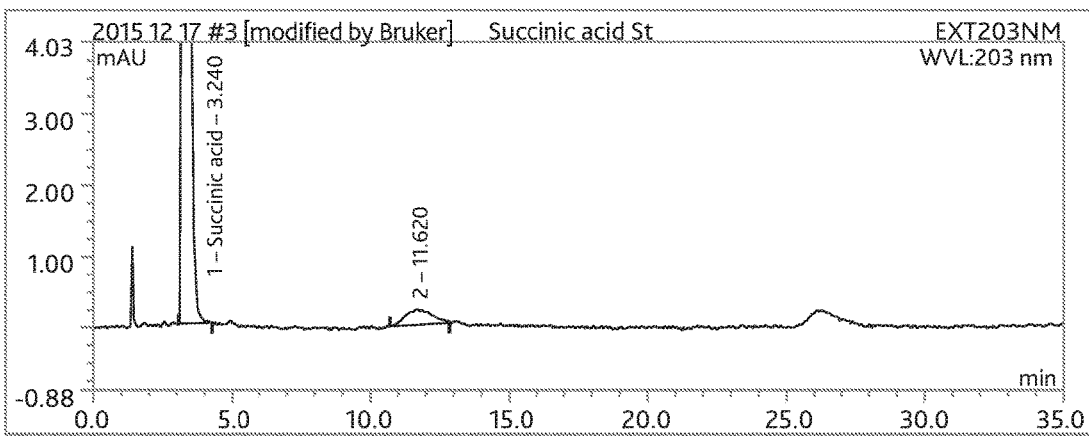

An aqueous mixture of cytisine and succinic acid was prepared. HPLC chromatograms for these starting materials are provided as FIGS. 1 and 2. Acetone was added, and cytisine succinate salt was isolated from the mixture at a yield of about 70%.

Figure 3A:
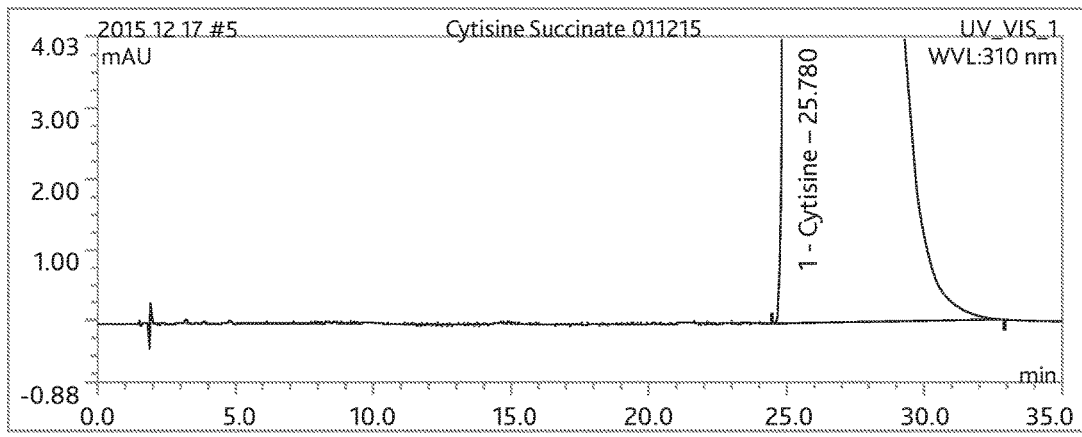
FIG. 3 shows HPLC chromatograms of cytisine succinate at (a) 310 nm and (b) 203 nm.
Figure 3B:
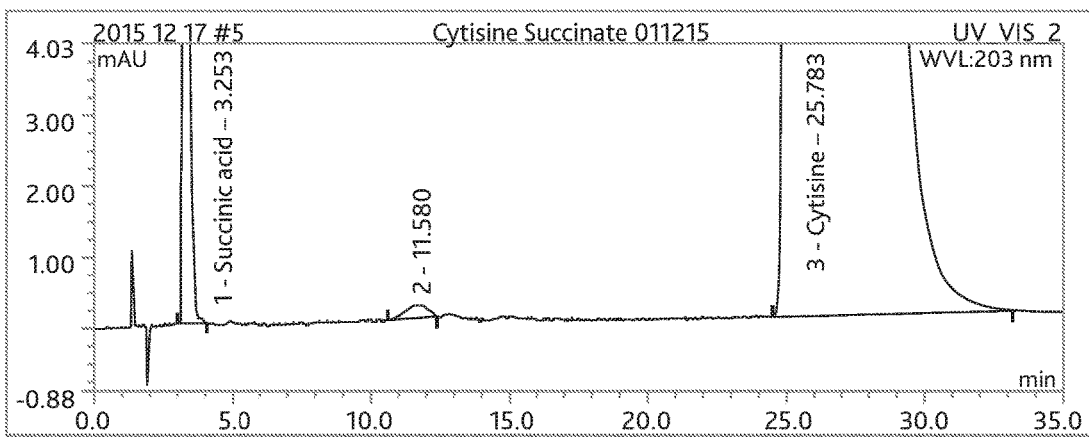
Figure 5A:
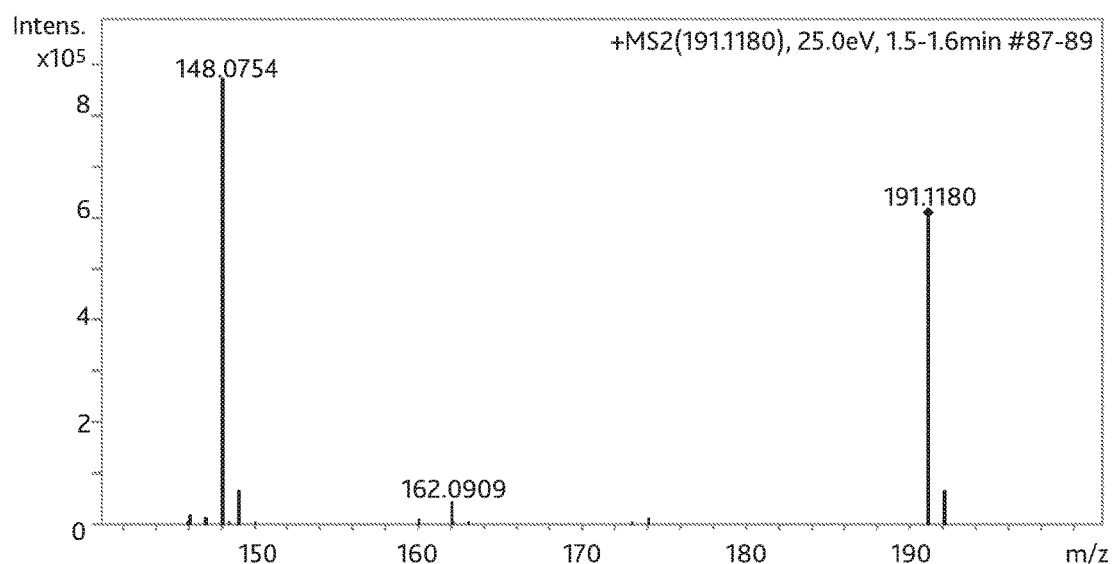
FIG. 5 shows the MS-MS spectra of cytisine succinate: (a) ESI+ and (b) ESI−
Figure 5B:
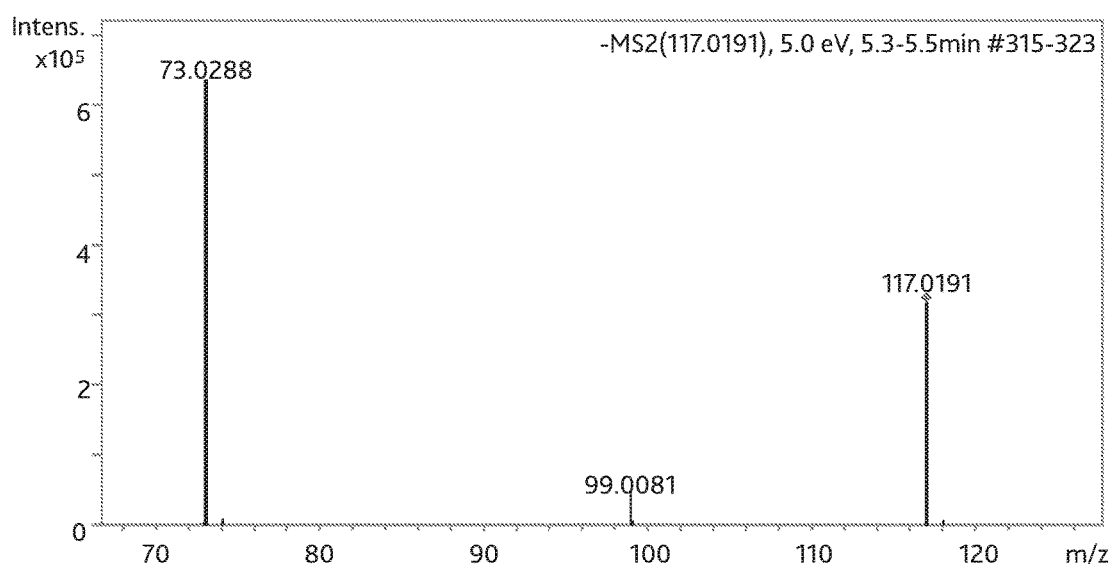
Figure 6A:
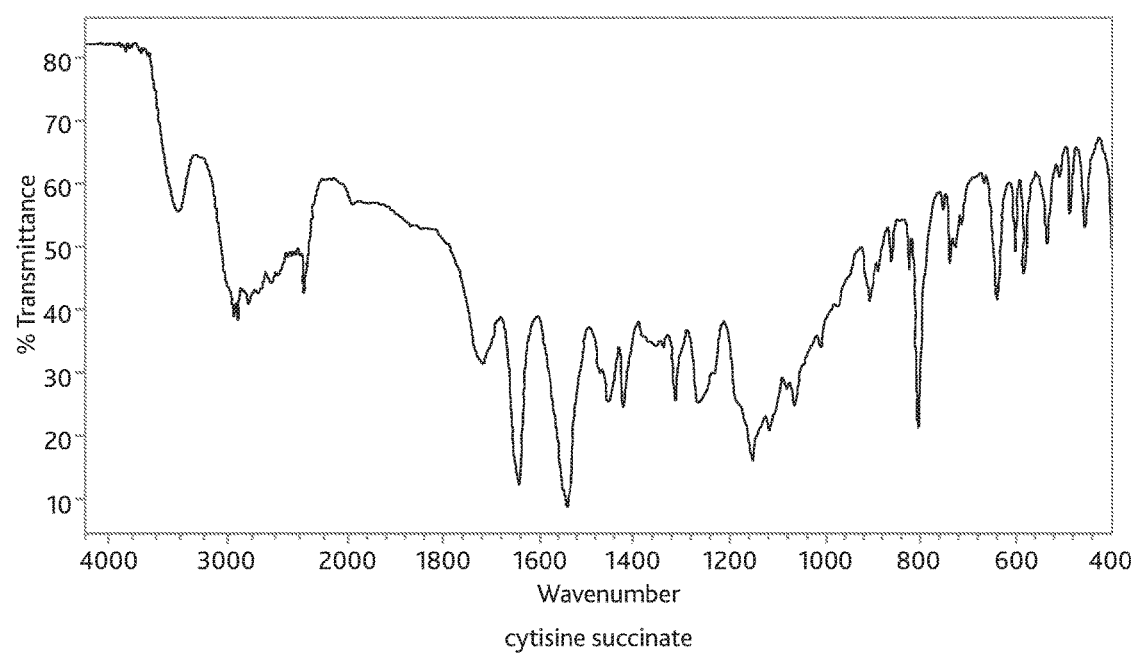
FIG. 6 shows the IR spectra of cytisine succinate: (a) FTIR and (b) FTIR (ATR)

The starting materials (cytisine and succinic acid) and the obtained salt were characterised using a number of analytical methods, see FIGS. 1 to 7. The results are presented in Table 1 below. Chromatographic purity of the salt was determined using HPLC and was found to be greater than 99.9% (FIG. 3). As can be seen, the salt of the present invention can be easily produced at very high levels of purity using conventional salification processes.

The obtained salt was also subjected to high resolution mass spectrum analysis (FIG. 4), tandem mass spectroscopy (FIG. 5), IR spectroscopy (FIG. 6) and UV/VIS analysis (FIG. 7) was performed.

TABLE 1

| No | Test items | Cytisine Succinate |
|---|---|---|
| | Characterisation tests | |
| 1 | Appearance | White crystals |
| 2 | UV/VIS (HPLC DAD) | |
| | UV/VIS Cytisine | Max. 232.3 nm; 304.7 nm |
| | UV/VIS Acid Anion | Max. 203.7 nm |
| 3 | IR | 2932 cm$^{-1}$; 2363 cm$^{-1}$; 1719 cm$^{-1}$; 1645 cm$^{-1}$; 1545 cm$^{-1}$; 1267 cm$^{-1}$; 1161 cm$^{-1}$; 805 cm$^{-1}$; 642 cm$^{-1}$ |
| 4 | HR MS (Q-TOF) | |
| | ESI+ | 191.1180 Cyt + H$^+$ |
| | | 381.2290 2Cyt + H$^+$ |
| | ESI− | 117.0195 Succ-H$^+$ |
| | | 99.0084 Succ-H$_2$O—H$^+$ |
| | | 73.0290 Succ-CO$_2$—H$^+$ |
| 5 | Chromatographic purity (HPLC DAD) | 310 nm > 99.9% |
| | | 203 nm > 99.9% |

EXAMPLE 2: STABILITY OF CYTISINE SUCCINATE SALT

Samples of cytisine succinate salt obtained from Example 1 were formulated in standard formulations to investigate their stability, and the compatibility of the API with the excipients used. Preliminary analysis of these formulations indicates that the formulations comprising succinate salt are significantly more stable than those comprising cytisine free base.

EXAMPLE 3—SALT SCREEN

Stock solutions of acid salt formers were prepared in the carrier solvents and having the molarities detailed in the following table:

| Acid | Solvent mix | Molarity |
|---|---|---|
| Acetate | EtOH | 1 |
| Ascorbate | 9:1 EtOH:water | 0.5 |
| Benzoate | EtOH | 1 |
| Succinate | EtOH | 0.5 |

Stock solutions of cytisine API (non-synthetic) were also prepared in CH$_3$CN and 2-Me-THF. 2.4 g of cytisine was dissolved in 24 ml of CH$_3$CN heated to a temperature of 40° C. 2.4 g of cytisine was dissolved in 60 ml of 2-Me-THF heated to a temperature of 60° C.

10 ml capacity tubes heated to 40° C. were charged with 2 ml of the cytisine/CH$_3$CN stock solution or 5 ml of the cytisine 2-Me-THF stock solution. The acid stock solutions were then added to the heated tubes in equimolar amounts. The solutions were held at 40° C. for one hour and then allowed to cool to ambient temperature (~18° C.) for 18 hours. Where solid formation did not spontaneously occur, manipulations were carried out, namely: i) gradual blow down under nitrogen to induce crystallisation, ii) charging antisolvent/triturate, and iii) second blow down under nitrogen and trituration with 3 ml TBME and 1 ml acetone.

Filtration of the obtained solids was then carried out using a PTFE fritted column and the obtained solids were dried at 50° C. for 48 hours. The properties of the obtained products were then analysed, and the following table summarises the outcome of this screen and the properties of the obtained products;

| API Stock Solution | Salt-type | Assessment |
|---|---|---|
| CH$_3$CN | Acetate | Base precipitation, unstable salt |
| 2-MeTHF | Acetate | Base precipitation, unstable salt |
| CH$_3$CN | Ascorbate | Base precipitation, unstable salt |
| 2-MeTHF | Ascorbate | Base precipitation, unstable salt |
| CH$_3$CN | Benzoate | Failed to yield solid |
| 2-MeTHF | Benzoate | Failed to yield solid |
| CH$_3$CN | Succinate | Excellent salt profile, mono succinate, reasonably high melt |
| 2-MeTHF | Succinate | Equivalent succinate to CH$_3$CN example with phase impurity/thermally induced modulation, possible polymorphism |

As can be seen, suitable salts could not be formed with the common acid salt formers acetic acid, ascorbic acid or benzoic acid. However, the succinate salt was readily formed, exhibiting advantageous properties.

EXAMPLE 4—LACTOSE INCOMPATIBILITY TESTING

Cytisine, 0.9541 g, was dissolved in water, 1 ml, and afforded a yellow solution. Succinic acid, 0.5919 g, 1 equiv, was charged as a solid to the cytisine solution and dissolved slowly with agitation. Acetone, 10 ml, was charged and afforded a partitioned mixture of cytisine/succinic acid/water solution, lower, and acetone, upper. Trituration of a portion of cytisine/succinic acid/water solution with acetone, 10 ml, converted the viscous mixture to a white solid which settled. The white suspension was charged to the remainder of the cytisine/succinic acid/water solution/acetone mixture with a rinse of acetone, 10 ml, and agitation continued. This converted the viscous cytisine/succinic acid/water mixture to a white suspension which settled when agitation was stopped. The solid was isolated by filtration and dried in vacuo at 50° C. for ca 16 hours. The recovered solid was confirmed as being cytisine succinate by $^1$H NMR analysis.

Recovery: 1.5463 g, 80.76% based upon a salt stoichiometry of cytisine to succinic acid of 1:1

The stability of cytisine/lactose and cytisine succinate/lactose binary mixtures was assessed at 40° C. and 75% relative humidity (RH) in vials with loosened lids at 9 days.

The sample mixtures and storage conditions used are detailed in Table 2 and Table 3.

TABLE 2

Cytisine/lactose mixtures and storage conditions

| No. | Cytisine, mg | Lactose, mg | Storage condition |
|---|---|---|---|
| 1 | 100.6 | 99.8 | 40° C. and 75% RH |

TABLE 3

| Cytisine succinate/lactose mixtures and storage conditions | | | |
|---|---|---|---|
| No. | Cytisine succinate, mg | Lactose, mg | Storage condition |
| 2 | 98.4 | 101.8 | 40° C. and 75% RH |

The chemical purity of a cytisine/lactose mixture was 99.83 area % and a cytisine succinate/lactose mixture was 99.68 area % at the start of the of the stability study.

Upon completion of the stability testing period, the following results were observed:

TABLE 4

| Characteristics of cytisine, cytisine succinate, cytisine/lactose and cytisine succinate/lactose stored for 9 days at 40° C. and 75% RH | |
|---|---|
| No. | CP of cytisine by HPLC, area % |
| 1 - Cytisine/lactose | 62.75 |
| 2 - Cytisine succinate/lactose | 77.47 |

As can be seen from the data in Table 4, when present in the form of its succinate salt, cytisine is degraded at a substantially lower rate than when present in free base form. Thus, the succinate salt effectively improves the stability of cytisine and facilitates its formulation with compositions comprising lactose.

The invention claimed is:

1. A succinate salt of cytisine.

2. The salt of claim 1, wherein the salt is cytisine hydrogen succinate.

3. A solvate or hydrate of the salt of claim 1.

4. A pharmaceutical composition comprising the salt of claim 1 and a pharmaceutically acceptable excipient.

5. The pharmaceutical composition according to claim 4, wherein the composition is in the form of a tablet or capsule.

6. The pharmaceutical composition according to claim 4, wherein the pharmaceutically acceptable excipient is selected from the group consisting of lactose, corn starch, wheat starch, and mixtures thereof.

7. The pharmaceutical composition according to claim 4, wherein the composition is provided as a unit dosage form.

8. The pharmaceutical composition according to claim 7, wherein the unit dosage form comprises 1 to 3 mg of a succinate salt of cytisine.

9. A method for treating nicotine addiction, comprising administering a therapeutically effective amount of a salt of claim 1 to a subject in need thereof.

10. A solvate or hydrate of the salt of claim 2.

11. A pharmaceutical composition comprising the salt of claim 2 and a pharmaceutically acceptable excipient.

12. The pharmaceutical composition according to claim 11, wherein the composition is in the form of a tablet or capsule.

13. The pharmaceutical composition according to claim 11, wherein the pharmaceutically acceptable excipient is selected from the group consisting of lactose, corn starch, wheat starch, and mixtures thereof.

14. The pharmaceutical composition according to claim 11, wherein the composition is provided as a unit dosage form.

15. The pharmaceutical composition according to claim 14, wherein the unit dosage form comprises 1 to 3 mg of cytisine hydrogen succinate.

16. A method for treating nicotine addiction, comprising administering a therapeutically effective amount of the salt of claim 2 to a subject in need thereof.

* * * * *